United States Patent
Carlson et al.

(10) Patent No.: US 8,741,621 B2
(45) Date of Patent: Jun. 3, 2014

(54) ENHANCED PRODUCTION AND PURIFICATION OF A NATURAL HIGH INTENSITY SWEETENER

(75) Inventors: Alfred Carlson, Terre Haute, IN (US); Richard W. Armentrout, Decatur, IL (US); Timothy Peter Ellis, Boxborough, MA (US)

(73) Assignee: Tate & Lyle Technology Limited, London (GB)

( * ) Notice: Subject to any disclaimer, the term of this patent is extended or adjusted under 35 U.S.C. 154(b) by 415 days.

(21) Appl. No.: 12/571,743

(22) Filed: Oct. 1, 2009

(65) Prior Publication Data

US 2010/0112639 A1    May 6, 2010

Related U.S. Application Data

(60) Provisional application No. 61/111,910, filed on Nov. 6, 2008.

(51) Int. Cl.
*C12N 15/79* (2006.01)
*C12R 1/84* (2006.01)
*A61K 38/00* (2006.01)

(52) U.S. Cl.
USPC ............. 435/235.1; 435/466; 435/252.3; 435/254.23; 435/255.5; 530/350

(58) Field of Classification Search
CPC ....... C12N 15/79; C12N 15/8257; C12R 1/84
See application file for complete search history.

(56) References Cited

U.S. PATENT DOCUMENTS

| | | | |
|---|---|---|---|
| 4,495,280 A * | 1/1985 | Bujard et al. | 435/6.14 |
| 5,326,580 A | 7/1994 | Hellekant et al. | |
| 5,346,998 A | 9/1994 | Hekllekant et al. | |
| 5,527,555 A | 6/1996 | Hellekant et al. | |
| 5,741,537 A | 4/1998 | Hellekant et al. | |
| 5,759,802 A * | 6/1998 | Maki et al. | 435/69.1 |
| 6,274,707 B1 | 8/2001 | Markley et al. | |
| 7,153,535 B2 | 12/2006 | Jin et al. | |
| 2007/0122895 A1 | 5/2007 | Raymond et al. | |
| 2009/0221078 A1* | 9/2009 | Caimi et al. | 435/471 |
| 2009/0311749 A1* | 12/2009 | Takagi et al. | 435/69.1 |
| 2010/0076176 A1* | 3/2010 | Miles et al. | 530/370 |
| 2011/0014650 A1* | 1/2011 | Young et al. | 435/69.1 |
| 2011/0021843 A1* | 1/2011 | Bailey et al. | 568/367 |

FOREIGN PATENT DOCUMENTS

| WO | WO 94/24280 | 10/1994 |
|---|---|---|
| WO | WO 99/25835 A1 | 5/1999 |

OTHER PUBLICATIONS

Sunga et al. (2004) The *Pichia pastoris* formaldehyde dehydrogenase gene (FLD1) as a marker for selection of multicopy expression strains of *P. pastoris*, Gene, vol. 330, pp. 39-47.*
Zhang et al. (2008) Study on the Synthesis of Sweet Protein Brazzein Gene and the Expression in the *Pichia pastoris*, Journal name "农产品加工 学刊", issue 10, pp. 4-7.*
Lamohear et al. (2005) Expression of the sweet protein brazzein in maize for production of a new commercial sweetener, Plant Biotech., vol. 3, pp. 103-114.*
Reference Invitrogen (2002) "pGAPZ A, B, and C", Version F, 25-0174, pp. 1-47.*
Al-Lian Zhang, et al., Recent Advances on the GAP Promoter Derived Expression System of *Pichia pastoris*, Molecular Biology Reports; An Internationall Journal on Molecular and Cellular Biology, Kluwer Academic Publishers, DO, vol. 36, No. 6, Sep. 10, 2008, pp. 1611-1619, XP019684802 ISSN: 1573-4978.
Masuda T., et al., High Yield Secretion of the Sweet-Tasting Protein Lysozyme from the Yeast *Pichia pastoris*, Protein Expression and Purificaton, Academic Press, San Diego, CA, vol. 39, No. 1, Jan. 1, 2005, pp. 35-42, XP004680014 ISSN: 1046-5928.
Narendar K. Khatri, et al., Oxygen-Limited Control of Methanol Uptake for Improved Production of a Single-Chain Antibody Fragment with Recombinant *Pichia pastoris*, Applied Microbiology and Biotechnology, Springer, Berlin, DE, vol. 72, No. 3, Mar. 11, 2006, pp. 492-498, XP019422027 ISSN: 1432-0614.
Theppanya Charoenrat, et al., Oxygen-Limited Fed-Batch Process: An Alternative Control for *Pichia pastoris* Recombinant Protein Processes, Bioprocess and Biosystems Engineering, Springer, Berlin, DE, vol. 27, No. 6, Oct. 1, 2005, pp. 399-406, XP019347364 ISSN: 1615-7605.
Görgens J. F. et al., Amino Acid Supplementation, Controlled Oxygen Limitation and Sequential Double Induction Improves Heterologous Xylanase Production by *Pichia stipitis*, Fems Yeast Research, Elsevier Science, Tokyo, NL, vol. 5, No. 6-7, Apr. 1, 2005, pp. 677-683, XP004789318 ISSN: 1567-1356.
Ouyang J, et al., High-Level Expression, Purification, and Characterization of Porcine Somatotropin in *Pichia pastoris*, Protein Expression and Purification, Academic Press, San Diego, CA, vol. 32, No. 1, Nov. 1, 2003, pp. 28-34, XP004469381 ISSN: 1046-5928.
Fariba M. Assadi-Porter, et al., Sweetness Determinant Sites of Brazzein, A Small, Heat stable, Sweet-Tasting Protein, Archives of Biochemistry and Biophysics, vol. 376, No. 2, Apr. 15, 2000, pp. 259-265.
Fariba M. Assadi-Porter, et al., Efficient Production of Recombinant Brazzein, a Small, Heat-Stable, Sweet-Tasting Protein of Plant Origin, Archives of Biochemistry and Biophysics, vol. 376, No. 2, Apr. 15, 2000, pp. 252-258.
Fariba M. Assadi-Porter, et al., Brazzein, A Small Sweet Protein: Effects of Mutations on Its Structure, Dynamics and Functional Properties, Chemical Senses, vol. 30, suppl 1, pp. i190-i191 (2005), Oxford University Press.
Jungoh Ahn, et al., Translation Elongation Factor 1-α Gene From *Pichia pastoris*: Molecular Cloning, Sequence, and Use of Its Promoter, Appl. Microbiol Biotechnol (2007), vol. 74, pp. 601-608.
Daniel M. Becker, et al., High-Efficiency Transformation of Yeast by Electroporation, Methods in Enzymology, vol. 194, (1991), pp. 182-187.

(Continued)

*Primary Examiner* — Karen Cochrane Carlson
*Assistant Examiner* — Samuel Liu
(74) *Attorney, Agent, or Firm* — RatnerPrestia (57) ABSTRACT

Recombinant *P. pastoris* producing natural sweet proteins and methods for engineering these recombinant yeast are described. Methods for enhancing foreign protein production in yeast fermentation and improved methods for purification of foreign proteins produced in yeast fermentation are presented.

14 Claims, 7 Drawing Sheets

(56) References Cited

OTHER PUBLICATIONS

James M. Cregg, et al., DNA-Mediated Transformation, Method in Molecular Biology, vol. 389, *Pichia* Protocols, Second Edition, pp. 27-41, (2007).

James M. Cregg, Distinctions Between *Pichia pastoris* and Other Expression Systems, Methods in Molecular Biology, vol. 389; *Pichia* Protocols, Second Edition, pp. 1-10, (2007).

Frank B. Dean, et al., Rapid Amplification of Plasmid and Phage DNA Using Phi29 DNA Polymerase and Multiply-Primed Rolling Circle Amplification, Molecular Staging Inc. , Amersham Pharmacia BiotechGenome Research, vol. 11, (2001), pp. 1095-1099.

Mehmet Inan et al., Saturation of the Secretory Pathway by Overexpression of a Hookworm (*Necator americanus*) Protein (Na-ASP1), Method for Molecular Biology, vol. 389, *Pichia* Protocols, Second Edition, pp. 65-75, (2007).

Zheyuan Jin, et al., Monkey Electrophysiological and Human Psychophysical Responses to Mutants of the Sweet Protein Brazzein: Delineating Brazzein Sweetness, Chemical Senses, vol. 28, (2003), pp. 491-498.

Kiran M. Khandke, et al., Influence of Ions on Cyclization of the Amino Terminal Glutamine Residues of Tryptic Peptides of Streptococcal PepM49 Protein, Int. J. Peptide Protein Res. vol. 34., (1998), pp. 118-123.

Yuan Yi Liu, et al., Targeted Introduction of a Diphtheria Toxin Resistant Mutation Into the Chromosomal EF-2 Locus of *Pichia pastoris* and Expression of Immunotoxin in the EF-2 Mutants, Protein Expression and Purification, vol. 30, (2003), pp. 262-274.

Yuan Yi Liu, et al., Overexpression of an Anti-CD3 Immunotoxin Increases Expression and Secretion of Molecular Chaperone BiP/Kar2p, Applied and Environmental Microbiology, Sep. 2005, pp. 5332-5340.

Joan Lin-Cereghino, et al., Vectors and Strains for Expression, Methods in Molecular Biology, vol. 389; *Pichia* Protocols, Second Edition, pp. 11-25, (2007).

Manuel Mansur, et al., Multiple Gene Copy Number Enhances Insulin Precursor Secretion in the Yeast *Pichia pastoria*, Biotechnology Letters, vol. 27, (2005), pp. 339-345.

Ding Ming, et al., Brazzein, A New High-Potency Thermostable Sweet Protein From *Pentadiplandra brazzeana* B., FEBS Letters, vol. 355, (1994), pp. 106-108.

João Ricardo Moreira De Almeida, et al., Molecular Characterization of the 3-phosphoglycerate Kinase Gene (PGKI) From the Methylotrophic Yeast *Pichia pastoris*, Yeast, vol. 22, (2005), pp. 725-737.

Koti Sreekrishna, et al., Strategies for Optimal Synthesis and Secretion of Heterologous Proteins in the Methylotrophic Yeast *Pichia pastoris*, Elsevier Science B.V., Gene, vol. 190, (1997), pp. 55-62.

Anthony Jay Sunga, et al., The *Pichia pastoris* Formaldehyde Gene (FLD1) as a Marker for Selection of Multicopy Expression Strains of *P. pastoris*, Elsevier B.V. Gene, vol. 330, (2004), pp. 39-47.

Xion, et al., Influence of Signal Peptide Sequences on the Expression of Heterogeneous Proteins in *Pichia pastoris*, vol. 35, No. 2, (2003), pp. 154-160 (w/English Abstract).

International Search Report Jan. 21, 2010.

* cited by examiner

SEQUENCE LISTING

<160> NUMBER OF SEQ ID NOS: 6

<210> SEQ ID NO 1
<211> LENGTH: 488
<212> TYPE: DNA
<213> ORGANISM: Pichia pastoris

<400> SEQUENCE: 1

```
tttttgtag    aaatgtcttg  gtgtcctcgt  ccaatcaggt  agccatctct  gaaatatctg    60
gctccgttgc   aactccgaac  gacctgctgg  caacgtaaaa  ttctccgggg  taaaacttaa   120
atgtggagta   atggaaccag  aaacgtctct  tcccttctct  ctccttccac  cgcccgttac   180
cgtccctagg   aaattttact  ctgctggaga  gcttcttcta  cggcccccctt gcagcaatgc   240 tcttcccagc   attacgttgc  gggtaaaacg  gaagtcgtgt  acccgaccta  gcagcccagg   300
gatggaaaag   tcccggccgt  cgctggcaat  aatagcgggc  ggacgcatgt  catgagatta   360 ttggaaaacca  ccagaatcga  atataaaagg  cgaacaccct  tcccaatttt  ggtttctcct   420
gacccaaaga   ctttaaattt  aatttatttg  tccctatttc  aatcaattga  acaactattt   480
cgaaacga                                                                488
```

<210> SEQ ID NO 2
<211> LENGTH: 57
<212> TYPE: DNA
<213> ORGANISM: Saccharomyces cerevisiae

<400> SEQUENCE: 2

```
atgagatttc   cttctatttt  tactgcagtt  ttgttcgctg  cctcttccgc  tttggct       57
```

<210> SEQ ID NO 3
<211> LENGTH: 165
<212> TYPE: DNA
<213> ORGANISM: Pentadiplandra brazzeana

<400> SEQUENCE: 3

```
caagataagt   gtaagaaggt  ttacgaaaat  tacccagttt  ctaagtgcca  acttgctaat    60
caatgcaatt   acgattgcaa  gcttgataag  catgctagat  ctggagaatg  cttttacgat   120
gaaaagagaa   atcttcaatg  tatttgtgat  tactgtgaat  actaa                    165
```

<210> SEQ ID NO 4
<211> LENGTH: 162

```
<212> TYPE: DNA
<213> ORGANISM: Pentadiplandra brazzeana

<400> SEQUENCE: 4
gataagtgta agaaggttta cgaaaattac ccagtttcta agtgccaact tgctaatcaa      60
tgcaattacg attgcaagct tgataagcat gctagatctg gagaatgctt ttacgatgaa     120
aagagaaatc ttcaatgtat ttgtgattac tgtgaatact aa                        162

<210> SEQ ID NO 5
<211> LENGTH: 98
<212> TYPE: DNA
<213> ORGANISM: Pichia pastoris

<400> SEQUENCE: 5
tcaagaggat gtcagaatgc catttgcctg agagatgcag gcttcatttt tgatactttt      60
ttatttgtaa cctatatagt ataggatttt ttttgtca                              98

<210> SEQ ID NO 6
<211> LENGTH: 2651
<212> TYPE: DNA
<213> ORGANISM: Pichia pastoris

<400> SEQUENCE: 6
ctcctgatga ctgactcact gataataaaa atacggcttc agaatttctc aagactacac      60
tcactgtccg acttcaagta tgacatttcc cttgctacct gcatacgcaa gtgttgcaga     120
gtttgataat tccttgagtt tggtaggaaa agccgtgttt ccctatgctg ctgaccagct     180
gcacaacctg atcaagttca ctcaatcgac tgagcttcaa gttaatgtgc aagttgagtc     240
atccgttaca gaggaccaat tgaggagct gatcgcaac ttgctcaagt tgtacaataa     300
tggtatcaat gaagtgattt tggacctaga tttggcagaa agagttgtcc aaaggatccc     360
aggcgctagg gttatctata ggaccctggt tgataaagtt gcatccttgc ccgctaatgc     420
tagtatcgct gtgcctttt cttctccact gggcgatttg aaaagtttca ctaatggcgg     480
tagtagaact gtttatgctt tttctgagac cgcaaagttg gtagatgtga cttccactgt     540
tgcttctggt ataatcccca ttattgatgc tcggcaattg actactgaat cgaactttc     600
tgaagatgtc aaaagttcc ctgtcagtga aattttgttg gcgtctttga ctactgaccg     660
ccccgatggt ctattcacta cttttggtgg ctgactcttct aattactcgt tgggcctggt     720
gtactcgtcc aaaaagtcta ttccggaggc tataaggaca caaactggag tctaccaatc     780
tcgtcgtcac ggtttgtggt ataaaggtgc tacatctgga gcaactcaaa agttgctggg     840
tatcgaattg gattgtgatg gagactgctt gaaatttgtg gttgaacaaa caggtgttgg     900
tttctgtcac ttggaacgca cttcctgttt tggccaatca aagggtctta gagccatgga     960
agccaccttg tgggatcgta agagcaatgc tccagaaggt tcttatacca acggttatt    1020
tgacgacgaa gttttgttga cgctaaaat tagggaggaa gctgatgaac ttgcagaagc    1080
taaatccaag gaagatatag cctgggaatg tgctgactta ttttattttg cattagttag    1140
atgtgccaag tacggtgtga cgttggacga ggtggagaga aacctggata tgaagtccct    1200
aaaggtcact agaaggaaag gagatgccaa gccaggatac accaaggaac aacctaaaga    1260
agaatccaaa cctaaagaag tccctcttga aggtcgtatt gaattgtgca aaattgacgt    1320
ttctaaggcc tcctcacaag aaattgaaga tgcccttcgt cgtcctatcc agaaaacgga    1380
acagattatg gaattagtca aaccaattgt cgacaatgtt cgtcaaaatg gtgacaaagc    1440
ccttttagaa ctaactgcca gtttgatgg agtcgctttg aagacacctg tgttagaagc    1500
```

```
tcctttccca gaggaactta tgcaattgcc agataacgtt aagagagcca ttgatctctc    1560
tatagataac gtcaggaaat tccatgaagc tcaactaacg gagacgttgc aagttgagac    1620
ttgccctggt gtagtctgct ctcgttttgc aagacctatt gagaaagttg gcctctatat    1680
tcctggtgga accgcaattc tgccttccac ttccctgatg ctgggtgttc ctgccaaagt    1740
tgctggttgc aaagaaattg tttttgcatc tccacctaag aaggatggta cccttacccc    1800
agaagtcatc tacgttgccc acaaggttgg tgctaagtgt atcgtgctag caggaggcgc    1860
ccaggcagta gctgctatgg cttacggaac agaaactgtt cctaagtgtg acaaaatatt    1920
tggtccagga aaccagttcg ttactgctgc caagatgatg gttcaaaatg acacatcagc    1980
cctgtgtagt attgacatgc ctgctgggcc ttctgaagtt ctagttattg ctgataaata    2040
cgctgatcca gatttcgttg cctcagacct tctgtctcaa gctgaacatg gtattgattc    2100
ccaggtgatt ctgttggctg tcgatatgac agacaaggag cttgccagaa ttgaagatgc    2160
tgttcacaac caagctgtgc agttgccaag ggttgaaatt gtacgcaagt gtattgcaca    2220
ctctacaacc ctatcggttg caacctacga gcaggctttg gaaatgtcca atcagtacgc    2280
tcctgaacac ttgatcctgc aaatcgagaa tgcttcttct tatgttgatc aagtacaaca    2340
cgctggatct gtgtttgttg gtgcctactc tccagagagt tgtggagatt actcctccgg    2400
taccaaccac actttgccaa cgtacggata tgcccgtcaa tacagcggag ttaacactgc    2460
aaccttccag aagttcatca cttcacaaga cgtaactcct gagggactga aacatattgg    2520
ccaagcagtg atggatctgg ctgctgttga aggtctagat gctcaccgca atgctgttaa    2580
ggttcgtatg gagaaactgg gacttattta attatttaga gattttaact tacatttaga    2640
ttcgatagat c                                                         2651
```

ENHANCED PRODUCTION AND PURIFICATION OF A NATURAL HIGH INTENSITY SWEETENER

BACKGROUND OF THE INVENTION

Brazzein encompasses a group of related sweet proteins extracted and purified from the fruit of the African plant, *Pentadiplandra brazzeana*. (Ming and Hellekant, *FEBS Lett.* 355: 106-108, 1994). Brazzein occurs in three naturally occurring forms, the amino acid sequences of which are known: Type I is 54 amino acids in length and has an N-terminal pyrrolidone carboxylic acid; Type II is 54 amino acids in length and has an N-terminal glutamine, and Type III is 53 amino acids in length and has an N-terminal aspartic acid (Assadi-Porter, et al., *Arch. Biochem. Biophys.* 376: 252-258, 2000). In addition to the natural forms of brazzein, variants of brazzein, i.e., mutated and recombinant proteins with varied sequences and properties, have been created by genetic engineering, such as those described in U.S. Pat. Nos. 5,326,580; 5,346,998; 5,527,555; 5,741,537; 7,153,535; 6,274,707 and in Jin, et al., *Chemical Senses* 28: 491-498; Assadi-Porter, et al., *Arch. Biochem. Biophys.* 376: 259-265, 2000; Assadi-Porter, et al., *Chem. Senses* 30 (*Suppl.* 1): i90-i91, 2005. Brazzein is a high-intensity natural sweetener, having an excellent taste profile, 400-500 times the sweetness of sucrose, and excellent stability at low pH and high temperatures.

Described below are methods, using food-grade methodology and yeast fermentation, for enhanced production and improved purification of a natural, high-quality brazzein protein that enable the commercial production of brazzein. This unique protein has applications as a sweetener in the baking, beverage, and table-top product industries.

SUMMARY OF THE INVENTION

Disclosed is an expression vector for the production of a brazzein protein by a yeast cell comprising at least two cassettes, each cassette comprising a promoter sequence, a secretion signal sequence, a brazzein protein reading frame sequence, and a termination sequence, wherein the at least two cassettes are present in an expression vector comprising an integration sequence for integration of the cassettes into the yeast genome at a specific site.

Also disclosed is a recombinant *P. pastoris* cell comprising at least two copies of a gene construct comprising a pGAP promoter sequence, a secretion signal sequence, a brazzein Type II or Type III protein reading frame sequence, and a termination sequence, wherein the copies of the gene construct are present at a preselected integration site within the *P. pastoris* genome.

A method for producing enhanced levels of a brazzein protein is presented, comprising the steps of
  a) transforming one or more cells of *P. pastoris* with the expression vector of claim 1;
  b) growing the transformed cell or cells in a fermentation medium under aerobic conditions, wherein the transformed cells produce enhanced levels of a brazzein protein compared with cells containing only one copy of the brazzein protein gene.

A method for enhancing production of a foreign protein in recombinant *Pichia* is presented, comprising the steps of
  c) initiating a culture of the recombinant *Pichia*, under aerobic conditions,
  d) reducing oxygen levels in the culture to less than 5%, and
  e) maintaining oxygen levels in the culture at less than 5%.

A method for purifying a protein from a yeast fermentation culture is also presented, comprising the ordered steps of a) adjusting the pH of the fermentation medium above or below the isoelectric point of the protein to be purified; b) removing the cells from the pH adjusted fermentation medium; c) subjecting the cell-free fermentation medium to ion-exchange chromatography and eluting the protein as a solution; d) passing the eluted protein solution through a first membrane to remove unwanted high molecular weight solutes; and e) concentrating and diafiltering the protein permeate on a second membrane to remove low molecular weight solutes.

DETAILED DESCRIPTION OF THE INVENTION

Genetic Enhancement of Brazzein Production

Genetic manipulation of *P. pastoris* uses a different set of techniques from those commonly used with bacteria. Foreign gene expression is engineered for stable integration by homologous recombination into specific sites in the host cell chromosome. These methods generally produce yeast cells that carry only one copy of the foreign gene. In some instances, foreign protein expression is enhanced by serendipitous integration of multiple gene copies in the yeast chromosome (Mansur, et al., *Biotech. Lett.* 27: 339-345, 2005; Sunga and Cregg, *Gene* 330: 39-47, 2004). However, this does not occur with all proteins and is unpredictable. Expression of integrated multiple gene copies depends on the toxicity of the foreign protein for the yeast, the ability of the cell to process the pre-protein, and other factors, such as those reviewed in Inan, et al., *Methods in Molec. Biol.* 389: 65-75, 2007). Production of a number of foreign proteins by *Pichia* has been shown to reach a limit as the gene copy number increases, primarily because cellular mechanisms for protein secretion become saturated (Liu, et al., *Appl. Environ. Microbiol* 71: 5332-5340, 2005; Dean, et al., *Genome Rsch.* 11: 1095-1099, 2001; Liu, et al., *Protein Expression and Purification* 30: 262-274, 2003). Therefore, it is not always possible to predict whether multi-copy integration will increase expression and secretion of a foreign protein in *Pichia* (Sreekrishna, et al., *Gene* 190: 55-62, 1997).

A reference *Pichia pastoris* strain, PB3, contains one copy of an artificial gene based on the amino acid sequence of Type II brazzein and optimized for yeast codon usage. The brazzein gene is under the control of the pGAP (glyceraldehyde-3-phosphate dehydrogenase) promoter of *Pichia pastoris*, allowing constitutive expression of the brazzein gene, and downstream of a 19 amino acid pre-sequence for *S. cerevisiae* MF-α (mating factor alpha), allowing secretion of the brazzein into the yeast medium. However, this yeast strain produces brazzein at insufficient levels for efficient commercial production.

Methods are described below that enhance the production of high levels of brazzein proteins by *P. pastoris* in large scale fermentation. The terms "enhanced production," "increased production," "enhanced yield," and "increased yield" as used herein mean that the amount of brazzein measured in the final *Pichia* fermentation broth by the "enhanced" or "increased" *Pichia* yeast production strain is greater than that of the reference strain, PB3.

Figure 1A:
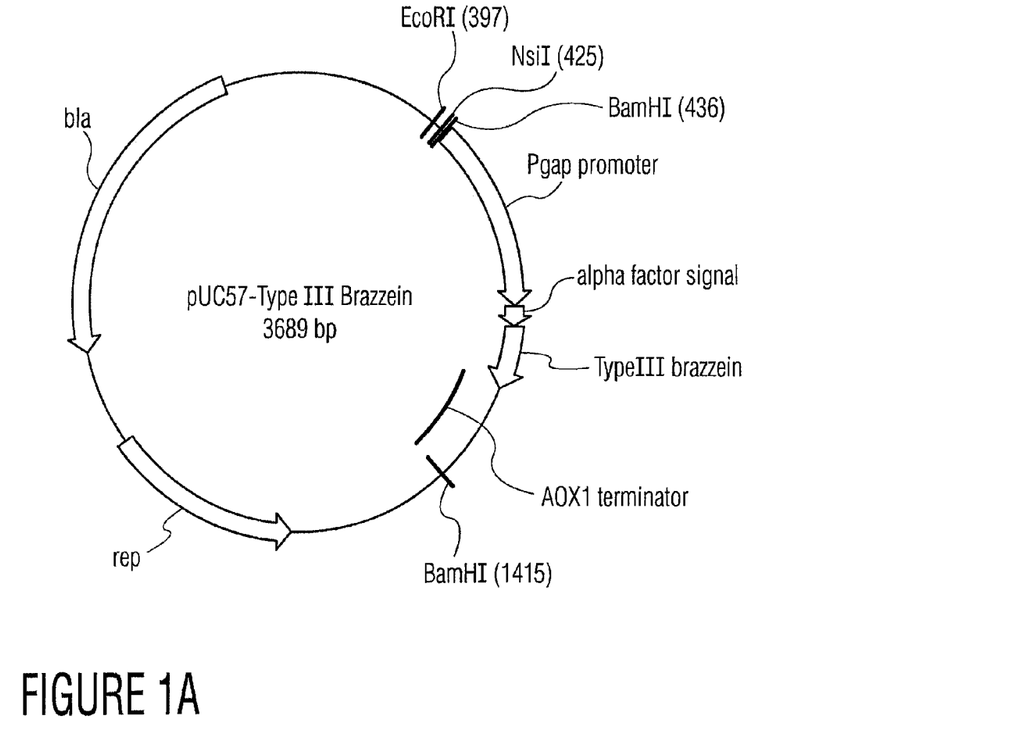
FIG. 1 shows the construction of an expression vector for brazzein for integration into the His 4 site of the *P. pastoris* genome.

One embodiment of a multi-gene construct that can be used to transform *P. pastoris* for enhanced production of brazzein is shown in FIG. 1A (FIG. 1 depicts Type III brazzein, but the same strategy can be used for the Type II brazzein gene). Bam H1 gene cassettes are designed to contain, in order from 5' to 3', the *P. pastoris* pGAP promoter, the 19 amino acid *S. cerevisiae* mating factor alpha pre-sequence, either the type II or type III brazzein gene and the AOX1 terminator, as shown in FIG. 1A. A small percentage of Type II brazzein is spontaneously converted to Type I brazzein in yeast fermentation cultures. However, Type I brazzein can be produced by chemically converting the N-terminal glutamine of Type II brazzein to pyroglutamate using standard methods, for example, as described in Khandke, et al., *Int. J. Peptide Protein Res.* 34: 118-123, 1989 or through enzymatic conversion, for example, with the Qcyclase™ enzyme from Qiagen.

While the pGAP promoter is preferred, other *P. pastoris* constitutive or inducible promoter sequences may be used, including, but not limited to, PPHIS4, FLD1, PEX 8, YPTI, as described in Sunga and Cregg, *Gene* 330: 39-47, 2004 and Lin-Cereghino, J and Lin-Cereghino, G P, *Methods in Molecular Biology* 389: 11-25, 2007, TEF1 (Ahn, et al., *Appl. Microbiol. Biotechnol.* 74: 601-608, 2007), and PGK1 (de Almeida, et al., *Yeast* 22: 725-737, 2005; WO/1994/24280). More than one type of promoter may be used in multi-copy constructs, e.g., the pGAP promoter with PGK1. Alternatively, hybrid promoters may be created using parts of different promoters.

Any leader signal sequence (pre-, pro-, or pre-pro), from *Pichia* or other organisms, that promotes secretion of brazzein can be used, such as the full length *S. cerevisiae* MF-α or other variations of the MF-α leader sequence; matrix metalloproteinase, PHO-1 and PHA-E leader sequences; and the β-glucanase leader sequence. (Xiong et al., *Acta Biochim. Biophys. Sinica* 35: 154-160, 2003; Sreekrishna, et al., *Gene* 190: 55-62, 1997; Lin-Cereghino, J and Lin-Cereghino, G P, *Methods in Molecular Biology* 389: 11-25, 2007; US2007/0122895).

In addition to AOX1, other terminator sequences can be utilized. For an appropriate promoter, such as those listed above (e.g., pGAP, PPHIS4, FLD1, PEX 8, or YPTI), the termination signal for the associated *P. pastoris* gene can be used. For example, the FLD1 promoter and terminator have been successfully used together as described by Sunga and Cregg, *Gene* 330: 39-47, 2004. Alternatively, terminator and promoter sequences from different genes may be paired in the construct.

Figure 1B:
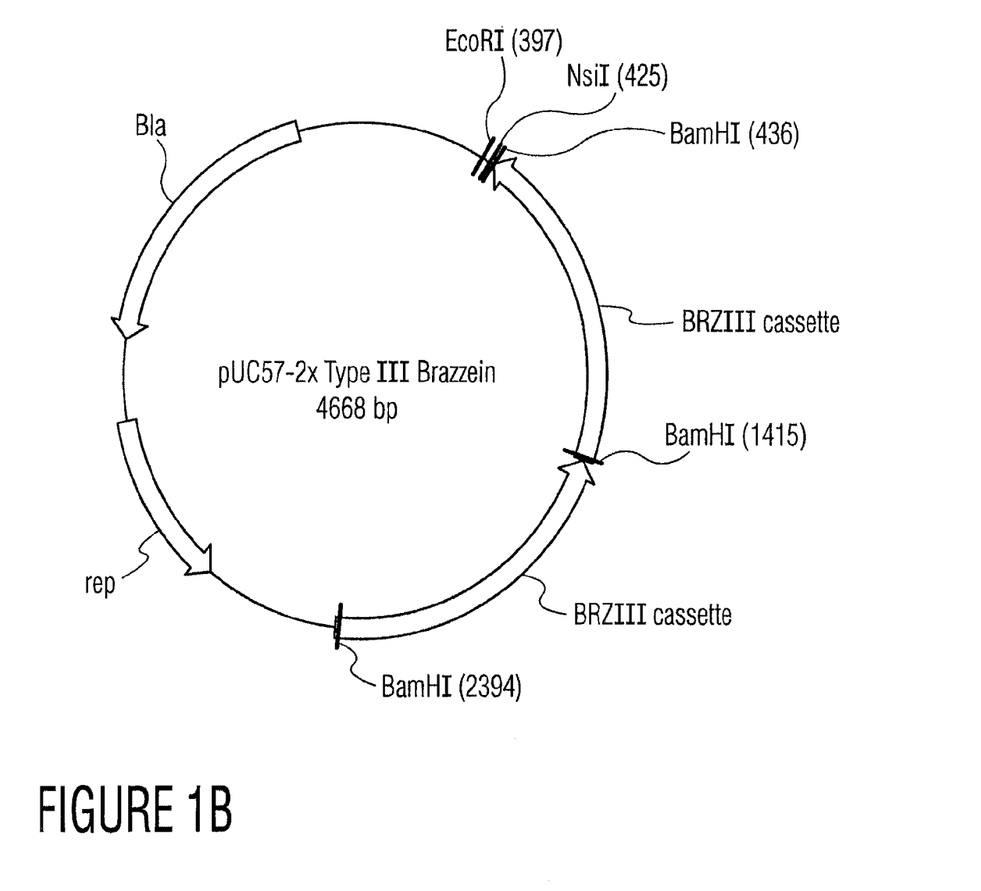

Multimeric brazzein cassettes are prepared by ligating copies of the Bam H1 fragments to each other. Ligations may be replicated, screened and characterized by any appropriate method, such as those described in Example 1. Following construction, the cassettes are then cloned into an expression plasmid or other vector from which the DNA can be easily amplified. Any appropriate vector carrying a selectable marker, e.g., antibiotic resistance, may be used. For example, the cassettes can be cloned into *E. coli* plasmid vectors and *E. coli* used to produce the DNA for transforming yeast cells. In the embodiment shown in FIG. 1B, ligation products with the desired number of brazzein cassettes were inserted into the Bam H1 site of pUC57, as described in Example 1. Alternatively, the DNA can be amplified in vitro, for example, as described by Dean, *Genome Res.* 11: 1095-1099, 2001, and used to transform yeast cells.

Figure 1C:
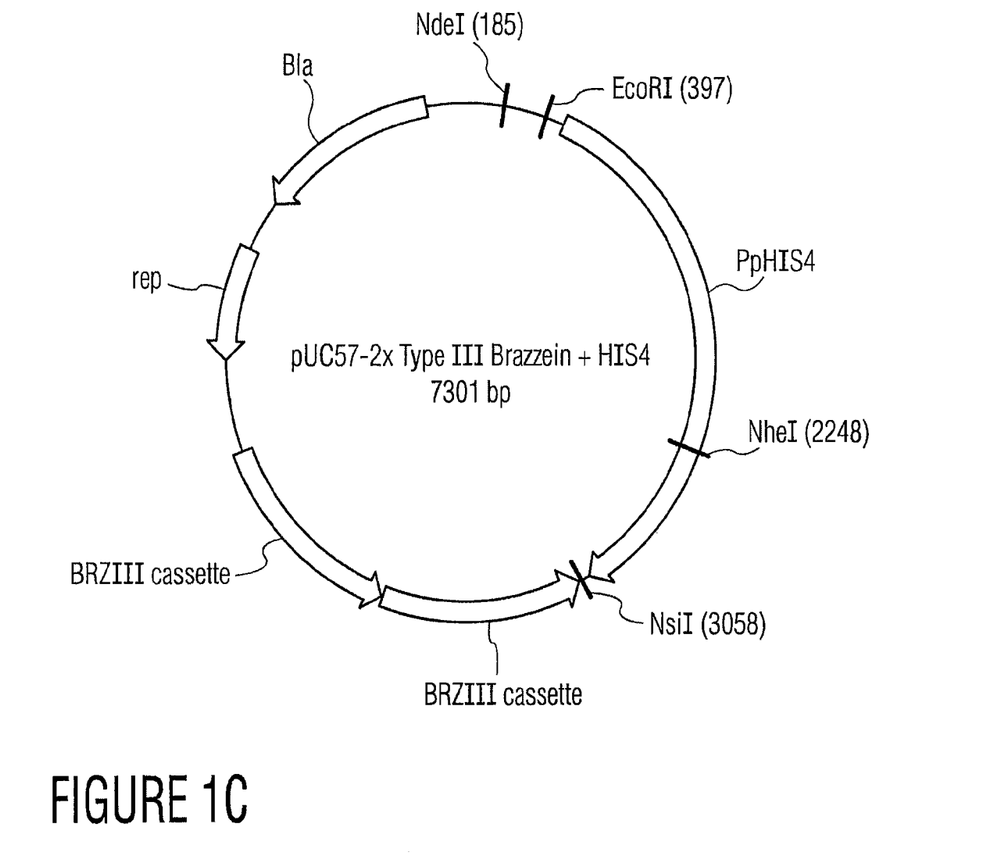

In one embodiment, an expression plasmid is created by inserting the *Pichia* histidine gene 4, PPHIS4, which includes the HIS4 reading frame, 84 base pairs of promoter sequence and 40 base pairs of terminator sequence, into the vector comprising the brazzein cassettes, (FIG. 1C). PPHIS4 allows integration of the foreign gene at the chromosomal HIS 4 site of *P. pastoris*. Any *P. pastoris* gene containing appropriate restriction sites can be used as a homologous recombination site for integration. Other possible integration sites include, but are not limited to, *P. pastoris* genes pGAP, AOX1, PHO1, and FLD1. The final expression plasmid is generally sequenced to confirm that the correct gene sequences are present.

Conventional methods of molecular biology are used to create the brazzein cassettes, plasmids, and expression vectors. Such methods are described, for example, in *Molecular cloning: a laboratory manual*, 3rd ed., Sambrook, Joseph; Russell, David W., New York: Cold Spring Harbor Laboratory, 2001; *Molecular Cloning: A laboratory manual*, 2d ed., Sambrook, J., Fritsch, E. F., and Maniatis, T. New York: Cold Spring Harbor Laboratory Press, 1989; Cold Spring Harbor Protocols, cshprotocols.cshlp.org; *Current Protocols in Molecular Biology*, currentprotocols.com.

The expression vectors are used to transform *P. pastoris*. Any appropriate method of transformation may be used including electroporation and chemical-mediated transformation as described, for example, in Cregg, *Methods in Molecular Biology* 389: 27-42, 2007 and in Becker and Guarenta, *Methods in Enzymology* 194: 182-187, 1991. Transformed yeast cells may be stored at −80° C. in a solution containing 10% glycerol.

Environmental Enhancement of Brazzein Production

The production of brazzein by *Pichia* yeast engineered to produce brazzein proteins under control of the pGAP promoter can, surprisingly, be regulated by controlling the availability of oxygen in the fermentation reactor. In general, fermentation cultures of *Pichia* are grown as fed batch cultures in 20-40% air saturation (0.04-0.09 mg/ml dissolved oxygen). As described in Examples 5 and 6 and shown in FIGS. 2-4, restricting available $O_2$ to less than about 5% air saturation causes a 2-2.5 fold increase in production and secretion of brazzein Type II (FIG. 2) and Type III (FIGS. 3 and 4).

No differences were observed in optical density (i.e., cell proliferation), $CO_2$ evolution, $O_2$ uptake, or glucose consumption between the control and oxygen stressed cultures. The yeast continue to grow aerobically in the low $O_2$ environment, and no changes in cell metabolism other than enhanced production of brazzein were observed. Although the exact mechanism for the oxygen stress effect is not known, it appears to have a specific effect on the synthesis of the foreign proteins. Secretion of the foreign proteins occurs at a maximal rate even at normal oxygen levels, as evidenced by the lack of accumulation of these proteins inside the yeast cells. While not excluding other hypotheses, it appears that oxygen stress affects the function of the pGAP promoter in *Pichia*. Therefore, the oxygen stress technique can be used to increase *Pichia* production of any foreign protein that is controlled by the pGAP promoter. Other promoters are likely to be stimulated by oxygen stress.

*Pichia* is one of the best organisms for large-scale production of foreign proteins, and genetic methods to enhance the production of foreign proteins in *Pichia* have been widely studied and are reviewed in Cregg, *Methods in Mol. Biol.* 389: 1-7, 2007. The pGAP promoter is a constitutive promoter native to *Pichia*. Standard methods of molecular biology, such as those described above and in Examples 1-4, may be used to clone a foreign protein with the pGAP promoter in an appropriate expression vector for production and secretion of the foreign protein under control of the pGAP promoter. *Pichia* cells are then transformed with the expression vector using any suitable method of transformation and grown in a fed-batch culture, such as that described in Example 5. Other methods of culture that avoid the production of ethanol may also be used, for example, a simple batch culture with glycerol as the food source, or a chemostat culture system. The yeast culture is usually maintained and fed until an upper limit of cell density corresponding to a wet (packed) cell volume that is 60% of the total fermentation volume is achieved.

Oxygen stress of the culture can be initiated at any time. Oxygen stress can be initiated by any means that maintains $O_2$ availability in the culture at less than 5%. In one embodiment, described in Example 5, oxygen stress was initiated during the last feed and was achieved by controlling the agitation speed of the culture. Oxygen availability can also be reduced by limiting the flow of air, manipulating the composition of the gas, altering the backpressure on the reactor, or, to some extent, by altering the feed rate of glucose.

Enhanced Purification of Secreted Proteins from Large-Scale Fermentation Broth

Figure 2:
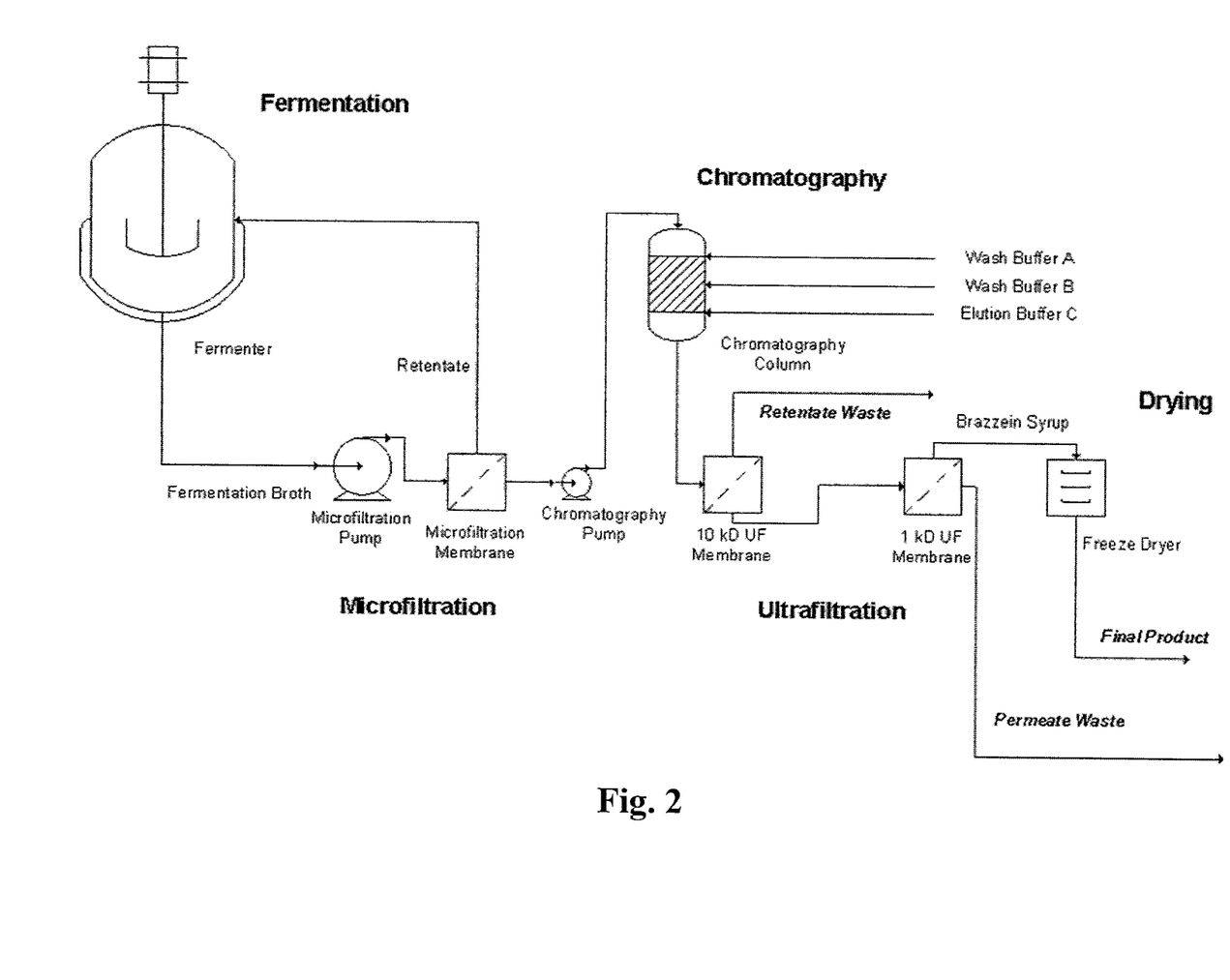
FIG. 2 is a schematic diagram of a process for purifying brazzein from fermentation medium.

High yields of purified protein can be obtained from large-scale yeast fermentations by following a series of ordered steps, which are shown schematically in FIG. 2. The process may be scaled to any size, so it can be used for any fermentation volume, and is suitable for any protein. *Pichia* is a preferred organism for production and secretion of foreign proteins into fermentation medium. *Pichia* will grow in a minimal salt medium, allowing filtration and chromatography at low conductivity. In addition, *Pichia* does not naturally secrete small proteins into the medium. Therefore, the only protein present in the medium in significant amounts will be the foreign protein to be purified and purification procedures can be optimized for that particular protein. One advantage of the process is that it does not utilize harsh chemical steps and can be employed in food production.

The first step of the process is performed before the yeast cells are removed from the broth. The pH of the fermentation medium is adjusted to create either a positive or negative charge on the protein to be purified. Thus, the pH of the medium will be below or above the isoelectric point (pI) of the protein for a positive or negative charge, respectively. Adjusting the pH as a first step reduces the need to dilute the micropermeate, thereby reducing the volume of material to be processed later through the ultrafiltration membrane. The second step is to remove the cells from the medium. This may be accomplished by any appropriate method including centrifugation, clarification, and microfiltration through filters with various pore sizes. For microfiltration processes, flux rates can be regulated to match the rate of flow through the chromatography column directly downstream of the membrane.

The permeate generated by microfiltration is pumped directly to a chromatography column. Any size column can be used and size selection is based on parameters known in the art, such as volume of permeate, capacity of column resin, rate, number of load-unload cycles desired, etc. Flow rate can be regulated by a feed pump that feeds the column, thereby also limiting the permeate flow rate from the microfiltration membrane. Any cation or anion exchange resin with a high capacity for the protein of interest at the pH of the permeate can be used. As the permeate runs through the column, the protein to be purified binds to the exchange resin while nucleic acids and polymers, carbohydrates, and most other proteins that may be in the cell broth pass through the column. When a sufficient volume of permeate has been generated, the feed of permeate to the chromatography column is stopped and the column is washed with several volumes of low salt buffer at a pH approximately that of the permeate to remove residual permeate from the column without removing bound protein. The column is then washed with several volumes of salt buffer having an intermediate molarity, e.g., 0.25-0.35M NaCl in 0.05 M acetate, at a pH approximately that of the permeate to remove bound proteins that are not the protein to be purified. After the washing steps, the column is eluted with a high salt buffer at a pH approximately that of the permeate to remove the bound protein to be purified. In lieu of a high salt elution buffer, the pH of the buffer can be raised or lowered to reverse the charge on the bound protein and release it from the resin. Wash and elution buffers and other column chromatography parameters can be optimized for specific proteins by methods known in the art, e.g., as described in Ion Exchange Chromatography & Chromatofocusing: Principles and Methods, GE Healthcare, www.4.gelifesciences.com/aptrix/upp00919.nsf/Content/71857706466D1AB8C1256EB400 41805D/$file/11000421AA.pdf (2004). The chromatography process removes most of the waste compounds generated during fermentation. This allows the subsequent ultrafiltration steps to run faster and minimizes the passage of contaminants into the ultrafiltration permeate.

The eluate is collected in fractions until all of the bound protein has been eluted. The process may be varied by using multiple columns, a simulated moving bed, or any appropriate modification. Fractions are assayed for protein according to known methods, e.g., absorbance at 280 nm, and fractions containing protein can be pooled for further purification. The pH of the protein-containing fractions may optionally be adjusted to a pH close to the pI of the protein to facilitate ultrafiltration at this step.

The protein fractions are next passed through a 5 to 30 kD nominal molecular weight cut-off (NMWCO) ultrafiltration membrane with a high volume of reverse osmosis purified (RO) water to remove co-eluted *Pichia* proteins. Any type of ultrafiltration membrane may be used. Such diafiltration methods and methods for optimizing diafiltration parameters are known in the art, e.g., as described in Technical Report PN33289, Pall Life Sciences, pall.com/pdf/02.0629_Buffer_Exchange_STR.pdf).

Following this first ultrafiltration step, the permeate is concentrated and diafiltered with a low NMWCO membrane, in general, 1 kD or less NMWCO. The protein is retained and salts and other low molecular weight contaminants pass through the membrane. The concentrated protein solution can then be diafiltered with water or buffers, if desired, to adjust the salt concentration in the concentrated solution. It may be desirable to again adjust the pH of the permeate prior to concentration to maintain high flux through the membrane and to prevent protein precipitation in the concentrated solution, as described in Example 9.

If desired, the concentrated solution of purified protein may be dried by any appropriate means such as oven drying, spray drying, and freeze drying for storage as a dry product.

In one embodiment of the process, the protein to be purified is brazzein. An exemplary process for purifying types I, II, and III brazzein is described in detail in Examples 7-9. For types I, II, and III brazzein, the pH of the fermentation medium is adjusted to 3.7-3.9 prior to removal of the yeast cells. A sample of the broth is assayed to estimate the concentration of protein in the broth. The fermentation broth is then pumped through a 2 m² microfiltration membrane (0.22 μm), at a rate appropriate for the estimated protein concentration, to remove cells. The permeate is then directly fed to a cation-exchange chromatography column. After completion of permeate input, the column is washed with a no salt and then low salt acetate buffer, pH about 3.8. Brazzein is eluted from the column with a high salt (1M NaCl), acetate (0.05 M) buffer, pH about 3.8. Following the chromatography step, the brazzein proteins are about 95% pure.

In this embodiment, the pH of the brazzein-containing fractions is adjusted to approximately 6.0-6.2 prior to concentration and ultrafiltration. A 10 kD NMWCO PES (polyethersulfone) filter is used to concentrate the volume of the brazzein-containing fractions. PES filters are preferred, because they do not exhibit changes in porosity, are easily cleaned and can be heat-sterilized. The solution is diafiltered to remove salts and buffer ions and the permeate is then concentrated and diafiltered a second time to flush the remainder of the brazzein through the membrane. The permeate is then concentrated with a 1 kD NMWCO PES filter which is then flushed with purified water. For Type III brazzein, the permeate from the 10 kD filter is adjusted to pH about 4.0 before concentration and filtration through the 1 kD filter membrane to prevent protein precipitation in the final concentrate. A fermentation volume of 620 L containing a mixture of Types I and II brazzein (about 280 g) yielded 4 L of solution containing about 260 g brazzein at 98% purity at the end of the purification process (Examples 7 and 8). For Type III brazzein, a fermentation volume of 600 L containing about 126 g of brazzein yielded 2 L containing about 99 g of Type III brazzein at 98% purity (Example 9). The final solution can be dried or filter-sterilized and stored as a solution.

EXAMPLES

1. Construction of a Multi-Cassette Expression Vector for Enhanced Expression of Brazzein Bam H1 brazzein gene cassettes were designed to comprise, in order from 5' to 3', the *P. pastoris* pGAP promoter (SEQ ID NO:1), the 19 amino acid *S. cerevisiae* alpha mating factor pre-sequence (SEQ ID NO:2), either the type II (SEQ ID NO:3 (includes stop codon)) or type III (SEQ ID NO:4) brazzein gene and the AOX1 terminator (SEQ ID NO:5), as shown in FIG. 1A. The brazzein cassettes were chemically synthesized and cloned into pUC57 by Integrated DNA Technologies, Coralville, Iowa.

Multimeric brazzein cassettes were prepared by excising the Bam H1 fragment by digestion with Bam H1, gel purifying the fragment, and ligating copies of the Bam H1 fragment to each other. The ligation reaction was purified and cloned into BamH1 linearized, dephosphorylated pUC57 using standard techniques of molecular biology. The resulting pUC57 vector (FIG. 1B) was used to transform stbl4 *E. coil* cells (Invitrogen). Transformants were identified on X-gal/IPTG spread LB+ampicillin plates by blue/white color selection. Positive colonies were confirmed by restriction digests of miniprep cultures. Because EcoRI and SalI cut to the outside of the BamHI sites, and EcoR1/SalI digest can be used to determine the number of brazzein copies present. BglII cuts near the 3' end of brazzein and a BglII digest can be used to determine the orientation of the cassettes relative to each other. Results suggest that only head-to-tail repeats are tolerated by the Stbl4 cells. The brazzein cassettes were sequenced to verify that the correct sequences were present.

To produce an expression plasmid, the *Pichia* histidine gene 4, PPHIS4, (SEQ ID NO: 6), which includes the HIS4 reading frame, 84 base pairs of promoter sequence and 40 base pairs of terminator sequence was cloned into the pUC57/Brazzein cassette construct (FIG. 1C).

An expression plasmid was produced for Type II brazzein with 4 copies of the brazzein Type II cassette. A Type III brazzein plasmid was produced with 2 copies of brazzein Type III cassette. Expression plasmids with greater numbers of copies of either the Type II or Type III brazzein gene could be made by ligating additional copies of the Bam H1 cassette together and inserting them collectively into a vector for yeast transformation.

2. Transformation of *P. Pastoris* with Brazzein Expression Plasmids

*P. pastoris* cells were transformed with the Type II or Type III brazzein expression plasmids of Example 1 via electroporation. Plasmids were cut with NheI to target insertion to the HIS4 site. Aliquots (40 μl) of competent *P. pastoris* cells suspended ice-cold 1M sorbitol were incubated with 10 μg of linearized plasmid DNA in an ice-cold 0.2 cm electroporation cuvette for 5 min on ice. Electroporation was performed using the following parameters: 25 μF, 200Ω, 2000 v. Immediately following electroporation, 1 mL of ice-cold 1M sorbitol was added and the contents transferred to a sterile 10 mL tube. The tube was incubated at 30° C. for 2 h then aliquots were spread onto BMDS plates (100 mM potassium phosphate, pH 6.0, 1.34% yeast nitrogen base without amino acids, 0.5% ammonium sulfate, $4 \times 10^{-5}$% biotin, 1M sorbitol, 2% dextrose, 2% agar). Plates were incubated for 4-5 days at 30° C.

In some instances, chemical transformation of *Pichia* was carried out using a commercial yeast transformation kit (EZ Yeast Transformation Kit, Zymo Research) according to manufacturer's instructions.

3. Identification of Transformed *P. pastoris*

Yeast colonies from Example 2 were grown for 48 h in 10 mL of YPD (yeast extract, peptone, dextrose) medium and transformants were identified by dot-blotting. Culture medium was centrifuged to remove cells and cell-free aliquots (2 μl) of full-strength and diluted (1:10) medium from each colony were blotted adjacent to each other onto a nitrocellulose membrane using a dot-blot filter apparatus. The membrane was blocked for 30 min with "blocking solution," (Western Breeze kit, Invitrogen). The membrane was then washed twice with water and incubated for 1 h in a 1:100,000 dilution of primary antibody (rabbit-anti-brazzein) capable of detecting Types I-III of brazzein in blocking medium. Following incubation with primary antibody, the membrane was then washed three times with "washing solution," (Western Breeze kit, Invitrogen), and incubated with a 1:10,000 dilution of secondary antibody (goat-anti-rabbit-HRP, Jackson Labs) for 30 min at room temperature. The membrane was subsequently washed three times with the washing solution and twice with water. A chromogenic substrate solution, (Western Breeze kit, Invitrogen), was applied to the membrane and incubated until a purple color developed (1-60 min). The membrane was again washed twice in water, air dried, and examined visually. Medium from colonies of yeast carrying multiple copies of the brazzein genes contained a noticeably higher amount of brazzein compared with the reference strain grown under identical conditions.

These results were confirmed and quantified by gel electrophoresis and HPLC. HPLC results for high-producing colonies are shown in Table 1.

4. Production of Brazzein Proteins by Recombinant *P. pastoris*

The transformed yeast of Example 3 were cultured in 1 L stir-tank reactors using a fed batch system with medium comprising basal salts and dextrose for about 60 h. Fermentation medium was analyzed for brazzein content by polyacrylamide gel electrophoresis and HPLC analysis. Cells were removed from the broth samples by centrifugation (3,000×g, 10 min, room temperature). The supernatant was diluted, filtered, and applied to a cationic HPLC column. The integrated peak eluting with an authentic brazzein sample was converted to mg/L using a standard of pure brazzein of known concentration. Results from the HPLC analysis are shown in Table 1. "Fold increase" is increase relative to the PB3 reference strain grown under the same conditions. The data show that the yeast with four copies of the Type II brazzein construct each secreted over four-fold greater amounts of Type II brazzein into the fermentation medium than the reference strain, PB3.

TABLE 1

Amount of Type II brazzein secreted into fermentation medium by recombinant *P. pastoris*

| Sample | mg/L Brazzein | Fold increase |
|---|---|---|
| PB3 | 82.7 | |
| PB3 duplicate | 87.9 | |
| PB3 duplicate | 75.9 | |
| Average PB3 | 82.0 | 1.0 |
| Type II 4x clone 2 | 198.3 | |
| Type II 4x clone 5 | 311.1 | |
| Type II 4x clone 8 | 507.2 | |
| Average Type II 4x clone | 338.9 | 4.1 |

5. Enhanced Production of Brazzein by Recombinant *P. pastoris*

Recombinant *P. pastoris* capable of expressing and secreting brazzein proteins were created as described in examples 1-4, and grown as high density, fed batch fermentation cultures. The recombinant yeast were added to a minimal yeast fermentation medium comprising glucose as the sole food source. Two, 10 L fermentation reactors were prepared by adding 1 L of 10× salts buffer containing 120 g/L of phosphoric acid and 25 g/L of $K_2SO_4$, to 6.5 L of reverse osmosis purified (RO) water. The reactor and contents were sterilized at 121° C. for 30 min. A sterile solution containing 2050 mL of 72% dissolved solids as 95% dextrose, 250 mL of a 500 g/L $MgSO_4$ (7H2O) solution, and 200 mL of trace metals with biotin was prepared. This solution (25 mL) was added to each fermentation tank, and the pH was adjusted to pH 5.6 with 28% $NH_4OH$.

Each reactor was inoculated with 100 mL of an overnight culture (O.D. ~5) of the recombinant *Pichia* cells. The yeast cells were allowed to grow overnight (about 16 h) until glucose in the medium was completely consumed. The medium was maintained at pH 5.6 and 30% air saturation (regulated by stirring).

The dextrose feed solution was pumped into the reactor at increasing rates (adjusted every 4 hours) until about 1 L had been added to each reactor (about 48 h). A sample was then taken from each reactor and brazzein levels in the medium were measured. The sample was filtered through a 0.22 μm filter and assayed on HPLC by ion exchange chromatography. The feed rate of the culture was increased to a final value of about 100 ml/h. This rate was continued until the culture was terminated (about 16 h).

In the "control" reactor the oxygen level was maintained at 30% by regulating the stirring rate. Table 2 lists the approximate feed and agitation rates over time for a 60 h, 10 L, control culture. In the "oxygen stress" reactor the agitation speed was locked at 750 RPM after reaching that rate of speed (Steps 7-8 of Table 2). In the oxygen stress reactor, oxygen levels dropped to as low as 3% during the last phase of the culture. Respiratory quotient was elevated about 5% under oxygen stress. Only minor differences were observed in optical density, $CO_2$ evolution, $O_2$ uptake, or consumption of base between the control and oxygen stress reactors.

TABLE 2

Simulated exponential fed batch culture for 10 L final volume process

| Step # | Feeding rate cc/hr | EFT hrs | Duration hours | RPM required (typical) | OD typical @ 660 nm |
|---|---|---|---|---|---|
| 0 | 0 | 0-16 | 16 | 150 | 2.5 |
| 1 | 5 | 16-20 | 4 | 250 | 4.2 |
| 2 | 8 | 20-24 | 4 | 280 | 7 |
| 3 | 12 | 24-28 | 4 | 320 | 12.6 |
| 4 | 18 | 28-32 | 4 | 350 | 20.6 |
| 5 | 30 | 32-36 | 4 | 450 | 31.3 |
| 6 | 48 | 36-40 | 4 | 550 | 54 |
| 7 | 80 | 40-44 | 4 | 700 | 82 |
| 8 | 100 | 44-60 | 16 | 1000 | 210 |

EFT—elapsed fermentation time

Figure 3A:
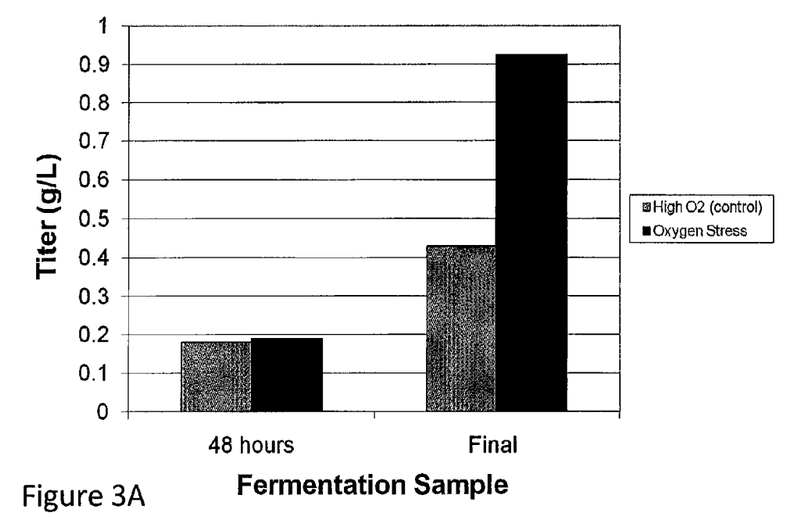
FIG. 3 is a graph showing the production of Type II brazzein by *P. pastoris* in 10 L reactor under oxygen stress. A. Raw data. B. Data normalized to optical density.
Figure 3B:
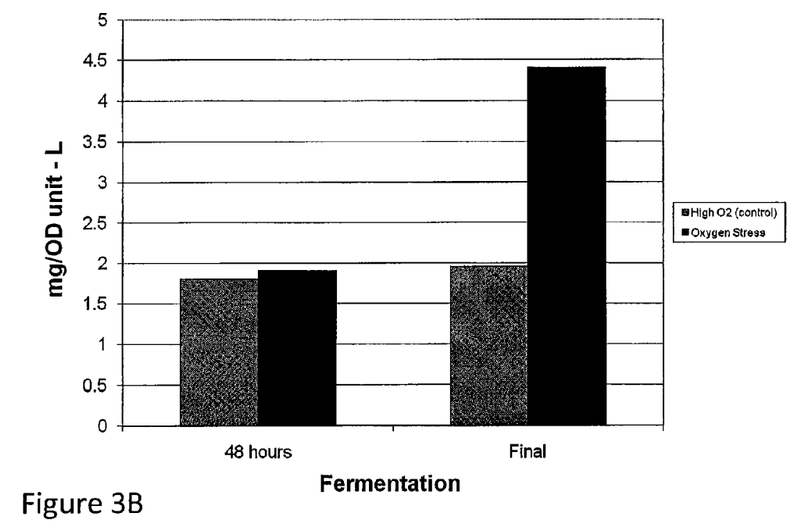

After all the glucose feed (2500 mL) had been added, samples of the medium were again taken and analyzed as described above to quantify brazzein in the cell-free broth. Results for cultures of *Pichia* expressing Type II brazzein are shown in FIG. 3 and for Type III brazzein in FIGS. 4 and 5. The amounts of Type II or Type III brazzein did not differ between the control and oxygen stressed reactors at 48 h, at which time conditions in each reactor were about the same. However, at the end of the culture (about 60 h), the amount of Type II brazzein in the oxygen stress reactor (~3% $O_2$) was approximately twice the amount of Type II brazzein in the control reactor (~30% $O_2$) as shown in FIG. 3A. On a per cell basis, *Pichia* cells produced about 2.2 times more Type II brazzein under oxygen stress conditions (FIG. 3B).

Figure 4A:
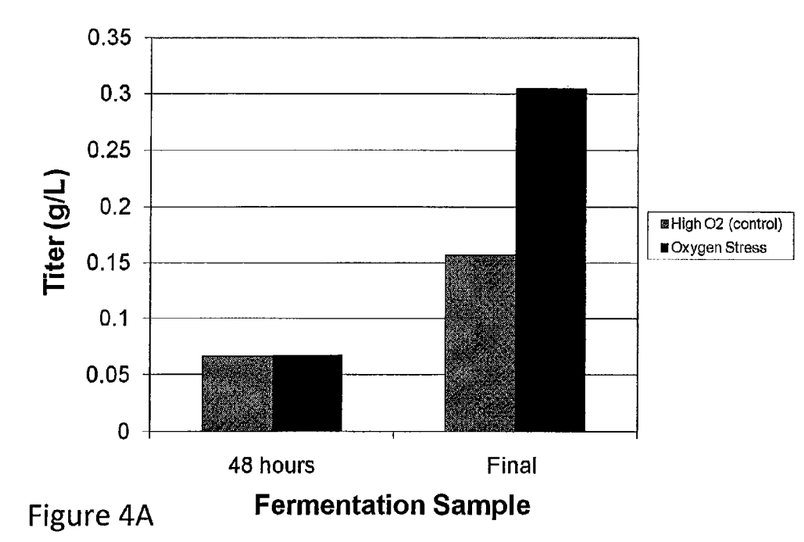
FIG. 4 is a graph showing the production of Type III brazzein by *P. pastoris* in a 10 L reactor under oxygen stress. A. Raw data. B. Data normalized to optical density.
Figure 4B:
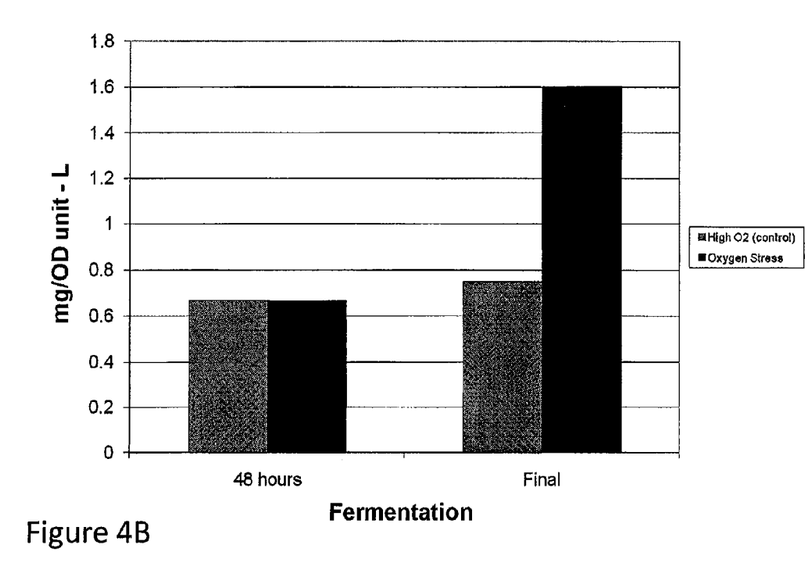

Similar results were obtained for *Pichia* producing Type III brazzein. Oxygen stressed reactors contained approximately twice the amount of Type III brazzein as the control reactors as shown in FIG. 4A. On a per cell basis, *Pichia* cells produced about 2.1 times more Type III brazzein under oxygen stress conditions (FIG. 4B).

Figure 5A:
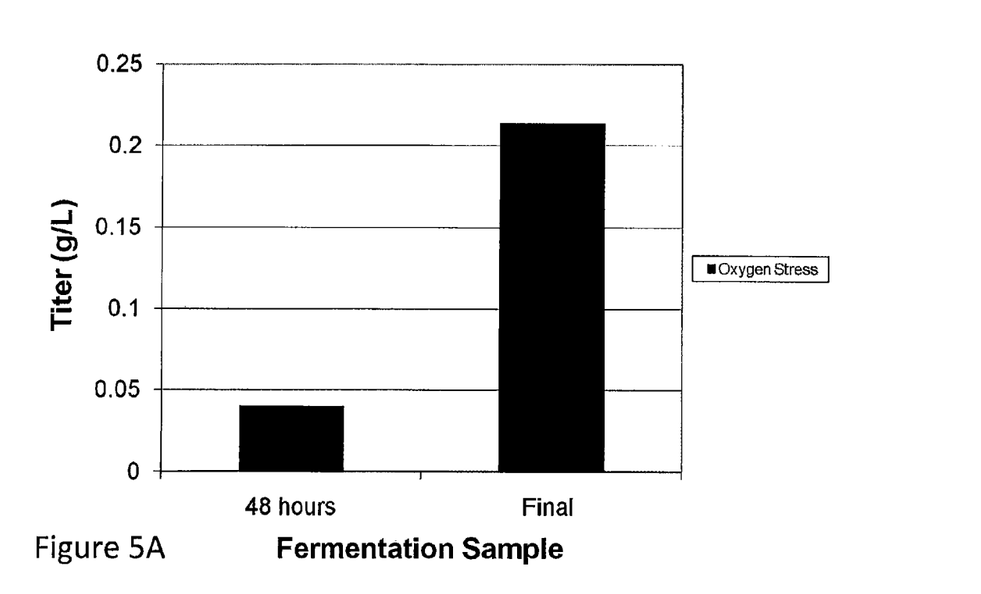
FIG. 5 is a graph showing the production of Type III brazzein by *P. pastoris* in a 1000 L reactor under oxygen stress. A. Raw data. B. Data normalized to optical density.
Figure 5B:
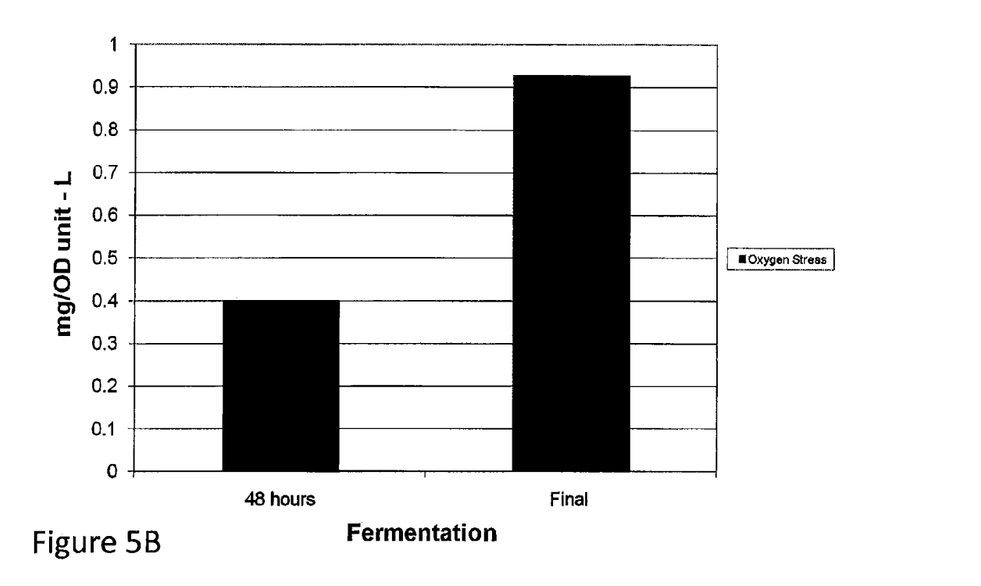

6. Effect of Oxygen Stress on Brazzein Production in Commercial Scale Fermentation The experiment described in the previous example was performed in a 1000 L fermentation reactor, i.e., a 100-fold scale-up of the process, with *Pichia* engineered to produce Type III brazzein. The reactors were maintained at 30% $O_2$ until 100 L of glucose had been added (agitation rate of about 250 RPM). At this time, the agitation rate was regulated to maintain $O_2$ at about 3% for the remainder of the culture. As shown in FIG. 5A, approximately 2.5 times more Type III brazzein was produced under oxygen stress conditions. FIG. 5B shows that this effect is due to increased *Pichia* productivity, as per cell production of Type III brazzein also increased about 2.5 fold.

7. Initial Purification of Type I and Type II Brazzein from Fermentation Medium

A 1000 L fermentation of *P. pastoris* carrying 4 copies of the type II brazzein gene was carried out as described in Example 5, but with MgSO$_4$ reduced by a factor of 5, at 30% dissolved oxygen. The pH of the medium was allowed to drop and was then maintained at 3.7-3.9 by addition of 12 N HCl. A sample of medium was filtered through a 0.22 μm filter and assayed by ion exchange HPLC. Peak areas corresponding to both Type II and Type I brazzein were found, as about 25% of Type II brazzein is, in general, spontaneously converted to Type I brazzein during culture. The titer of total brazzein protein was estimated to be about 0.45 g/L of cell free broth. This estimate extrapolates to an estimated 280 g total brazzein in the fermentation.

Whole cell broth was pumped out of the reactor into a 2 m$^2$ microfiltration membrane (0.22 μm, Millipore Duropore membrane) at a feed rate of about 45 LPM with a centrifugal pump. The feed pressure was about 37 psig and the retentate pressure was about 16 psig. Retentate was recycled back to the reactor. The permeate was pumped to a Waters Quickscale column containing 5 L Toyopearl SP550C (Tosoh Bioscience) cation-exchange chromatography column at 1 LPM. After about 8 h the permeate input to the column was stopped and the column was first washed with four volumes (20 L) of 0.005M acetate buffer, pH 3.8 (+/−0.1), and then washed with 20 L of 0.25 M NaCl in 0.05 M acetate buffer, pH 3.8. After washing, the column was eluted with 20 L of 1 M NaCl in 0.05 M acetate buffer, pH 3.8. Eluate was collected in 1 L fractions and each was assayed for brazzein. The column was flushed with eluting buffer and then washed with RO water. Significant amounts of brazzein were found only in the first 11 liters of eluate, and peak levels were found at 10 liters. The results of the assays are shown in Table 3. A total of 160-170 g of brazzein was collected. Type I brazzein eluted early and later fractions contained primarily Type II brazzein.

TABLE 3

First elution of brazzein from ion-exchange column

| Fraction Number | Elution Volume (Liters) | Brazzein Concentration (grams/Liter) |
|---|---|---|
| 1 | 4 | 2.1 |
| 2 | 5 | 18.0 |
| 3 | 6 | 17.9 |
| 4 | 7 | 19.3 |
| 5 | 8 | 22.4 |
| 6 | 9 | 27.9 |
| 7 | 10 | 31.7 |
| 8 | 11 | 28.7 |
| 9 | 12 | 9.0 |
| 10 | 13 | 2.0 |
| 11 | 14 | 0.5 |

The permeate line was reconnected to the column and the process was continued for another 12 h. The column was washed and eluted as described above and an additional 8 L of eluate containing brazzein were collected. An additional 110-120 g brazzein was collected (Table 4). The brazzein collected from the column in both elutions was about 95% pure as determined by absorbance at 280 nm.

TABLE 4

Second elution of brazzein from ion-exchange column

| Fraction Number | Elution Volume (Liters) | Brazzein Concentration (grams/Liter) |
|---|---|---|
| 1 | 3 | 1.3 |
| 2 | 4 | 19.2 |
| 3 | 5 | 66.8 |
| 4 | 6 | 25.5 |
| 5 | 7 | 1.8 |
| 6 | 8 | 0.4 |
| 7 | 9 | 0.3 |
| 8 | 10 | 0.2 |

8. Further Purification of Type I and Type II Brazzein

The purified brazzein from Example 7 was subjected to a two-step filtration process to remove salts and buffer ions. First, fractions were pooled to yield batches containing approximately 60-80 g of brazzein. The pH of each batch was adjusted with 1 N NaOH to 6.0-6.2. A 10 kD PES filter, operating at 30-40 psid, was then used to concentrate the volume of solution to about 2.5 L. The solution was then diafiltered with 20 L of RO water and the permeate collected. The permeate was again concentrated and diafiltered to flush the remainder of the brazzein through the membrane and into the permeate. Little or no brazzein was found in the retentate.

The permeate was concentrated to 500 mL with a 1 kD PES filter cartridge and the system was flushed with 500 mL of RO water. Samples were assayed for brazzein. In general, less than 5% of the brazzein was lost to the 1 kD permeate and 95% was recovered in the retentate. The complete purification process and results are summarized in Table 5. A final yield of approximately 260 g of brazzein was recovered at 98% purity.

TABLE 5

Type I and II Brazzein yields through purification process

| Step | Concentration | Amount | Purity | Volume |
|---|---|---|---|---|
| Fermentation | 0.45 g/L | 280 g | <10% | 620 L |
| Column Elution | 14.00 g/L | 280 g | 95% | 20 L |
| 10 kD permeate | 2.00 g/L | 280 g | 98% | 140 L |
| 1 kD concentrate | 65.00 g/L | 260 g | 98% | 4 L |

9. Purification of Type III Brazzein from Recombinant *P. Pastoris*

The purification process described in Examples 7 and 8 was carried out with 1000 L fermentation medium from a culture of *P. pastoris* carrying two copies of the gene for Type III brazzein. At the end of the fermentation, the pH of the medium was adjusted to about 3.8. An assay of a filtered sample of the medium indicated that the reactor contained about 126 g of brazzein. The medium was passed through a 2 m$^2$ microfiltration cartridge as described above, but at a permeate rate of about 1 LPM. The flow rate of permeate was maintained for about 22 h.

The permeate was passed directly through a 5 L column of SP 550C resin. The column was then washed and eluted as described in Example 7, but the NaCl concentration in the second wash buffer was 0.35 M instead of 0.25 M. Eluate was collected in 1 L bottles and assayed by A280 for total protein and by HPLC for brazzein.

Elution samples were adjusted to pH 6.1 (+/−0.1) with 1 N NaOH. Two groups of 6 bottles each were processed through a 10 kD NMWCO PES filter and diafiltered with about 40 L of RO water in two steps to produce a permeate containing substantially all of the brazzein. This permeate was collected from the membrane, adjusted to pH 4.0 (+/−0.2) using 1 N HCl, concentrated to 1 L using a 1 kD membrane, and subsequently diafiltered with about 10 L RO water. Diafiltration was continued until conductivity reached about 250 μS/cm or less. The solution was then allowed to concentrate to about 500 mL and the system was flushed with 500 mL of RO water. The liquid product was freeze dried to below 5% moisture. The results of this purification are shown in Table 6. Final yield was 2 L containing approximately 99 g of 98% pure Type III brazzein.

TABLE 6

Type III Brazzein yields through purification process

| Step | Concentration | Amount | Purity | Volume |
|---|---|---|---|---|
| Fermentation | 0.21 g/L | 126 g | <10% | 600 L |
| Column Elution | 10 g/L | 120 g | 95% | 12 L |
| 10 kD permeate | 1.25 g/L | 100 g | 98% | 80 L |
| 1 kD concentrate | 49 g/L | 99 g | 98% | 2 L |

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An expression vector for the production of a brazzein protein by a yeast cell, the expression vector comprising at least two cassettes, each cassette comprising a promoter, a secretion signal sequence, an open reading frame sequence encoding a brazzein protein, and a terminator, wherein the expression vector further comprises an integration sequence for integration of the cassettes at the corresponding chromosomal site of said integration sequence in the yeast genome, wherein the integration sequence comprises a HIS4 reading frame.

2. The expression vector of claim 1, wherein the yeast cell is from the genus *Pichia*.

3. The expression vector of claim 1, wherein the open reading frame sequence encoding the brazzein protein encodes a brazzein Type II or a brazzein Type III protein.

4. The expression vector of claim 1, wherein the promoter is a constitutive promoter.

5. The expression vector of claim 1, wherein the promoter is the pGAP promoter.

6. The expression vector of claim 1, wherein the promoter is selected from the group of promoters consisting of PPHis4, FLD1, PEX8, YPTI, TEF1, and PGK1.

7. The expression vector of claim 1, wherein the promoter and terminator are from the same gene.

8. The expression vector of claim 1, wherein the terminator is a terminator from a gene selected from the group consisting of AOX1, pGAP, PPHis4, FLD1, PEX8, and YPTI.

9. The expression vector of claim 1, wherein the secretion signal sequence is selected from the group consisting of the *S. cerevisiae* mating factor alpha signal sequence and a truncated form of the *S. cerevisiae* mating factor alpha signal sequence.

10. A recombinant *P. pastoris* cell comprising at least two copies of a gene construct comprising a pGAP promoter sequence, a secretion signal sequence, an open reading frame sequence encoding a brazzein Type II or a brazzein Type III protein, and a terminator, wherein the copies of the gene construct are present at a preselected integration site within the *P. pastoris* genome, wherein the copies of the gene construct are integrated from an expression vector comprising an integration sequence that corresponds with the sequence of the preselected integration site within the *P. pastoris* genome, wherein the integration sequence comprises a HIS4 reading frame.

11. A method for producing enhanced levels of a brazzein protein comprising the steps of a) transforming one or more cells of *P. pastoris* with the expression vector of claim 1; and b) growing the transformed cell(s) in a fermentation medium under aerobic conditions, wherein the transformed cell(s) produces enhanced levels of a brazzein protein compared with cells containing only one copy of the brazzein protein gene.

12. The method of claim 11, wherein the transformed cell(s) is grown in a fed-batch fermentation culture.

13. The method of claim 11, wherein the transformed cell(s) produces a protein selected from the group consisting of Type I brazzein, Type II brazzein, and Type III brazzein.

14. The method of claim 11, wherein the transformed cell(s) produces a variant of a Type I, II, or III brazzein protein.

* * * * *